US006642066B1

(12) United States Patent
Halliyal et al.

(10) Patent No.: US 6,642,066 B1
(45) Date of Patent: Nov. 4, 2003

(54) INTEGRATED PROCESS FOR DEPOSITING LAYER OF HIGH-K DIELECTRIC WITH IN-SITU CONTROL OF K VALUE AND THICKNESS OF HIGH-K DIELECTRIC LAYER

(75) Inventors: Arvind Halliyal, Cupertino, CA (US); Farzad Arsania, San Mateo, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/145,942

(22) Filed: May 15, 2002

(51) Int. Cl.$^7$ .......................... H01L 21/00; H01L 21/31; H01L 21/469
(52) U.S. Cl. .............................. 438/16; 438/7; 438/785; 356/369
(58) Field of Search ................................ 438/758, 785, 438/7, 16; 356/364, 369, 625, 635

(56) References Cited

U.S. PATENT DOCUMENTS

| | | | |
|---|---|---|---|
| 4,834,539 A | 5/1989 | Le Bris et al. | 356/369 |
| 5,181,080 A | 1/1993 | Fanton et al. | 356/381 |
| 5,625,455 A | 4/1997 | Nash et al. | 356/369 |
| 6,141,103 A | 10/2000 | Pinaton et al. | 356/369 |
| 6,207,589 B1 * | 3/2001 | Ma et al. | 438/785 |
| 6,222,199 B1 | 4/2001 | Freeouf | 250/559.27 |
| 6,233,046 B1 | 5/2001 | Alba et al. | 356/38 |
| 6,304,326 B1 | 10/2001 | Aspnes et al. | 356/369 |
| 6,323,947 B1 | 11/2001 | Freeouf | 356/369 |
| 6,429,943 B1 * | 8/2002 | Opsal et al. | 356/625 |
| 2001/0042832 A1 | 11/2001 | Herzinger et al. | 250/341.4 |

OTHER PUBLICATIONS

Johs et al, Recent Developments in SE for In Situ Applications, pp. 41–51, 2001.*
Johs et al.; "Recent Developments in Spectroscopic Ellipsometry for in situ Applications"; *Optical Metrology Roadmap for the Semiconductor, Optical, and Data Storage Industries II;* Vol 4449 (2001); pp. 41–57.
Hilfiker et al.; "Automated Spectroscopic Ellipsometry"; *The Industrial Physicist;* 1996 American Institute of Physics. (4 pp.).
"Optical Characterization of thin layers by spectroscopic ellipsometry"; Department of MOS System Studies of IET. (22 pp.; date unknown; printed Mar. 5, 2002 from web site http.//www.ite.waw.pl/department/zll/vase.html).

* cited by examiner

*Primary Examiner*—Alexander Ghyka
(74) *Attorney, Agent, or Firm*—Renner, Otto, Boisselle & Sklar, LLP (57) ABSTRACT

An apparatus and a method of depositing a dielectric material film, including steps of initiating a process of depositing a dielectric material film under at least one controllable initial condition in an apparatus comprising a dielectric material deposition chamber and a spectroscopic ellipsometer; and measuring, by the spectroscopic ellipsometer, at least one ellipsometric parameter of the dielectric material film during the process of depositing the film.

21 Claims, 3 Drawing Sheets

INTEGRATED PROCESS FOR DEPOSITING LAYER OF HIGH-K DIELECTRIC WITH IN-SITU CONTROL OF K VALUE AND THICKNESS OF HIGH-K DIELECTRIC LAYER

TECHNICAL FIELD

The invention relates generally to the fabrication of semiconductor devices and, more particularly, to the fabrication of a dielectric material film for use in semiconductor devices.

BACKGROUND ART

Fabrication of a semiconductor device and an integrated circuit thereof begins with a semiconductor substrate and employs film formation, ion implantation, photolithography, etching and deposition techniques to form various structural features in or on a semiconductor substrate to attain individual circuit components which are then interconnected to ultimately form an integrated semiconductor device. Escalating requirements for high densification and performance associated with ultra large-scale integration (ULSI) semiconductor devices requires smaller design features, increased transistor and circuit speeds, high reliability and increased manufacturing throughput for competitiveness. As the devices and features shrink, and as the drive for higher performing devices escalates, new problems are discovered that require new methods of fabrication or new arrangements or both.

There is a demand for large-scale and ultra large-scale integration devices employing high performance metal-oxide-semiconductor (MOS) devices. MOS devices typically comprise a pair of ion implanted source/drain regions in a semiconductor substrate and a channel region separating the source/drain regions. Above the channel region is typically a thin gate dielectric material, usually referred to as a gate oxide, and a conductive gate comprising conductive polysilicon or another conductive material. In a typical integrated circuit, a plurality of MOS devices of different conductivity types, such as n-type and p-type, and complementary MOS (CMOS) devices employing both p-channel and n-channel devices are formed on a common substrate. MOS technology offers advantages of significantly reduced power density and dissipation as well as reliability, circuit performance and cost advantages.

The drive towards increased miniaturization and the resultant limits of conventional gate oxide films have served as an impetus for the development of newer, high dielectric constant K ("high-K") materials as substitutes for conventional silicon dioxide-based gate oxide films. Since the drain current in a MOS device is inversely proportional to the gate oxide thickness, the gate oxide is typically made as thin as possible commensurate with the material's breakdown field and reliability.

Decreasing the thickness of the gate oxide film between the gate electrode and the source/drain extension regions, together with the relatively high electric field across the gate oxide film, can undesirably cause charge carriers to tunnel across the gate oxide film.

This renders the transistor "leaky", degrading its performance. To alleviate this problem, high-K dielectric materials are used as the gate insulator. Herein, a high-K gate oxide may be referred to as a high-K gate dielectric material film, in order to emphasize that the gate dielectric comprises a high-K dielectric material rather than silicon dioxide.

Using a high-K dielectric material for the gate dielectric film provides a low electrical thickness to be achieved while retaining a physically thick film. For example, a high-K gate dielectric with a K of 40 and a thickness of 100 angstroms is substantially electrically equivalent to a silicon dioxide gate dielectric (K about 4) having a thickness of about 10 angstroms. The electrically equivalent thickness of high-K materials may be referred to in terms of the equivalent oxide thickness of a film of silicon dioxide. Thus, a high-K dielectric film having K value of 40 and a given physical thickness has an equivalent oxide thickness which is approximately $\frac{1}{10}$ the given physical thickness. For higher-K dielectric materials, even thicker gate dielectric material films can be formed while maintaining equivalent oxide thickness values lower than are reliably and practically possible with very thin silicon dioxide films. In this way, the reliability problems associated with very thin dielectric films may be avoided while transistor performance is increased.

High-K dielectric materials may be used in many semiconductor devices, including for example, SONOS-type devices such as the MIRRORBIT™ flash memory cell available from Advanced Micro Devices, Inc., Sunnyvale, Calif., and in floating gate flash memory cells.

One problem which has been encountered in fabricating semiconductor devices including high-K dielectric materials is dimensional control, particularly being able to obtain a desired thickness and a desired K value of high-K dielectric materials. Since obtaining a given equivalent oxide thickness depends upon both the physical thickness and the K value of the dielectric material, control of these parameters is needed. It would be highly advantageous to develop a process that would permit close control of the thickness of high-K dielectric material films which are applied in semiconductor devices, and for this control to be available during the deposition of the dielectric material films, i.e., in situ. In addition, it is advantageous to develop methodologies capable of optimum fabrication processes for such devices. Accordingly, there exists a need for a process of manufacturing semiconductor devices with a high-K dielectric material film that improves process control of the quality, thickness and K value of dielectric material films, and particularly in high-K dielectric material films, while avoiding unduly expensive and time-consuming post-process physical measurement and/or electrical testing of such dielectric films.

DISCLOSURE OF INVENTION

The present invention relates to a method of depositing a dielectric material film, including steps of initiating a process of depositing a dielectric material film under at least one controllable initial condition in an apparatus comprising a dielectric material deposition chamber and a spectroscopic ellipsometer; and measuring in situ, by the spectroscopic ellipsometer, at least one ellipsometric parameter of the dielectric material film during the process of depositing the film.

In another embodiment, the present invention relates to a process for depositing a high-K dielectric material on a semiconductor substrate, including steps of providing an apparatus comprising both a device for depositing a dielectric material and a device configured to measure in situ at least one ellipsometric parameter relating to at least one of refractive index and dielectric constant of the dielectric material; placing a semiconductor substrate into the apparatus; depositing on the semiconductor substrate a film comprising a high-K dielectric material; measuring, during the depositing step, the ellipsometric parameter relating to at least one of refractive index and dielectric constant of the dielectric material film; and controlling, during the depositing step, at least one process parameter relating to the depositing step based on the ellipsometric parameter relating to at least one of refractive index and dielectric constant of the dielectric material film.

In one embodiment, the present invention relates to an apparatus including a first device for depositing a dielectric material; a second device configured to measure in situ at least one ellipsometric parameter relating to at least one of refractive index and dielectric constant of the dielectric material during deposition of the dielectric material in the first device; a processor for receiving the at least one ellipsometric parameter from the second device and outputting information relating to at least one process parameter; and a controller for receiving information from the processor and adjusting operating conditions of the first device based on the information relating to the at least one process parameter. The apparatus may be used to carry out the methods of the present invention.

The present invention, while primarily for use with high-K dielectric materials, is broadly applicable to deposition of any dielectric materials, including both standard-K dielectric materials and high-K dielectric materials. Thus, standard-K dielectric materials are included within the definition of "dielectric materials" as used herein.

Thus, the present invention provides an apparatus and a control process which provides for precise, in-situ control and determination of the quality, thickness and K value of a film of a dielectric material, in particular of a high-K dielectric material, and which overcomes the problem of expensive and time-consuming physical measurement and electrical testing to determine the quality, thickness and K value of such films after completion of the deposition steps.

It should be appreciated that for simplicity and clarity of illustration, elements shown in the figures have not necessarily been drawn to scale. For example, the dimensions of some of the elements are exaggerated relative to each other for clarity. Further, where considered appropriate, reference numerals have been repeated among the figures to indicate corresponding elements.

MODES FOR CARRYING OUT THE INVENTION

As used herein, the term "standard-K dielectric material" refers to a dielectric material having a K up to about 10. Such standard-K dielectric materials include, for example, silicon dioxide, which has a K of about 4, silicon oxynitride, which has a K of about 4–8 depending on the relative content of oxygen and nitrogen, and silicon nitride, which has a K of about 6–9, and aluminum oxide, which has a K of about 10.

As used herein, the term "high-K dielectric material" refers to a dielectric material having a K greater than about 10. Such high-K dielectric materials include, for example, $HfO_2$, $ZrO_2$ and others known in the art, some of which are specifically identified more fully below. In general, the term "high-K dielectric material" encompasses binary, ternary and higher oxides and any ferroelectric material having a K of about 10 or more. High-K dielectric materials may also include, for example, composite materials such as hafnium silicate, which has a K of about 14, and hafnium silicon oxynitride, which has a K of about 16, depending on the relative content of oxygen and nitrogen, and hafnium silicon nitride, which has a K of about 18.

As used herein, the term "composite dielectric material" refers to a dielectric material comprising the elements of at least two other dielectric materials. A composite dielectric material generally has a K value as defined above for a high-K dielectric material, and is included in the definition of high-K dielectric materials for purposes of the present disclosure. The definition is broad enough to include composite dielectric materials having K values less than 10. As described in more detail below, a composite dielectric material may be formed by co-deposition of its component elements, or by sequential deposition followed by a treatment step, e.g., thermal treatment, to combine the elements to form the composite dielectric material.

High-K Dielectric Materials

Approximate K-values or, in some cases, a range of K-values, are shown below in Table 1 for several exemplary dielectric materials. It is understood that the present invention is not limited to the specific dielectric materials disclosed herein, but may include any appropriate standard-K, high-K and composite dielectric materials which are known and are compatible with the remaining elements of the semiconductor device with which the dielectric materials are to be used.

TABLE 1

| Dielectric Material | Approximate Dielectric Constant (K) (Relative Permittivity) |
| --- | --- |
| silicon dioxide | 4 |
| silicon nitride | 6–9 |
| silicon oxynitride | 4–8 |
| aluminum oxide | 10 |
| zirconium silicate | 12 |
| hafnium silicate | ~10–30 |
| hafnium aluminate | ~12–30 |
| lanthanum oxide, $La_2O_3$ | 20–30 |
| hafnium oxide, $HfO_2$ | 20 |
| zirconium oxide, $ZrO_2$ | 25 |
| cerium oxide, $CeO_2$ | 26 |
| bismuth silicon oxide, $Bi_4Si_2O_{12}$ | 35–75 |
| titanium dioxide, $TiO_2$ | 30 |
| tantalum oxide, $Ta_2O_5$ | 26 |
| tungsten oxide, $WO_3$ | 42 |
| yttrium oxide, $Y_2O_3$ | 20 |
| $LaAlO_3$ | 25 |
| BST ($Ba_{1-x}Sr_xTiO_3$) | ~20—200 |
| $PbTiO_3$ | ~20—200 |
| $BaTiO_3$ | ~20—200 |
| $SrTiO_3$ | ~20—200 |
| $PbZrO_3$ | ~20—200 |
| PST ($PbSc_xTa_{1-x}O_3$) | ~200—3000 |
| PZN ($PbZn_xNb_{1-x}O_3$) | ~200—5000 |

TABLE 1-continued

| Dielectric Material | Approximate Dielectric Constant (K) (Relative Permittivity) |
|---|---|
| PZT ($PbZr_xTi_{1-x}O_3$) | ~100—1000 |
| PMN ($PbMg_xNb_{1-x}O_3$) | ~200—5000 |

It is noted that the K-values, or relative permittivity, for both standard-K and high-K dielectric materials may vary to some degree depending on the exact nature of the dielectric material and on the process used to deposit the material. Thus, for example, differences in purity, crystallinity and stoichiometry, may give rise to variations in the exact K-value determined for any particular dielectric material.

As used herein, when a material is referred to by a specific chemical name or formula, the material may include non-stoichiometric variations of the stoichiometrically exact formula identified by the chemical name. For example, hafnium oxide, when stoichiometrically exact, has the chemical formula $HfO_2$. As used herein, the term "hafnium oxide" may include variants of stoichiometric $HfO_2$, which may be referred to as $Hf_xO_y$, in which either of x or y vary by a small amount. For example, in one embodiment, x may vary from about 0.75 to about 1.5, and y may vary from about 1.5 to about 3. In another embodiment, x may vary from about 0.9 to about 1.2, and y may vary from about 1.8 to about 2.2. Such variations from the exact stoichiometric formula fall within the definition of hafnium oxide. Similar variations from exact stoichiometry are included when the chemical formula for a compound is used. For example, again using hafnium oxide as an example, when the formula $HfO_2$ is used, $Hf_xO_y$ as defined above, is included within the meaning. Thus, in the present disclosure, exact stoichiometry is intended only when such is explicitly so stated. As will be understood by those of skill in the art, such variations may occur naturally, or may be sought and controlled by selection and control of the conditions under which materials are formed.

Here and in all numerical values in the specification and claims, the limits of the ranges and ratios may be combined.

Refractive Index and Dielectric Constant

As in known in the art, the refractive index and the permittivity of a material have the following relationship:

$$\epsilon = N^2 = (\eta + ik)^2$$

where $\epsilon$ is the permittivity, N is the complex index of refraction, $\eta$ is the real index of refraction and k is the extinction coefficient. Thus, if the refractive index can be determined empirically, the permittivity can be calculated from the above equation.

Permittivity, $\epsilon$, of a material reflects the ability of the material to be polarized by an electric field. The permittivity of a material is typically described as its permittivity normalized to the permittivity of a vacuum, $\epsilon_0$. Hence, the relative permittivity, referred to as the dielectric constant, of a material is defined as:

$$K = \epsilon/\epsilon_0$$

In one embodiment of the present invention, based on the relationship between refractive index and dielectric constant, if the refractive index of a variety of materials of known composition are determined, measurement of the refractive index of a material allows a person or a computer processor to look up from a table or other stored information the dielectric constant, K, of the material of interest. In another embodiment, the method is used to detect changes in K, based on changes in the refractive index, N. In another embodiment, the actual or absolute value of K is not determined, but the refractive index, N, is tracked for changes, based on the understanding that changes in refractive index may reveal changes in K. Thus, it may not be necessary to determine accurately the absolute value of the K of the film formed in the process. As described more fully below, the ellipsometric parameters obtained are used to control the process of formation of the dielectric material. These are highly useful procedures, since determination of the actual K value of a dielectric material used in semiconductor devices is difficult, owing among other things to the small size of the components.

Spectroscopic Ellipsometry

In one embodiment, the optical characterization of dielectric material films, such as high-K dielectric material films, can be determined by use of a spectroscopic ellipsometer. Any spectroscopic ellipsometer, suitably designed for use in conjunction with the deposition process with which it is coupled, may be employed in carrying out the present invention. In one embodiment, the spectroscopic ellipsometer is capable of operating at variable angles. For example, a variable angle spectroscopic ellipsometer (VASE®) from J. A. Woollam Co., Inc. may be used. The present invention is not limited to use of any particular spectroscopic ellipsometer.

Spectroscopic ellipsometry techniques are based upon the fact that a linearly-polarized light vibration may be resolved into two perpendicular vibrations that are in phase. One of these vibrations is in the incidence plane and the other is in a plane normal to the incidence plane. After reflection or transmission, these vibrations undergo amplitude and phase changes which are generally different. Thus, after reflection, the light is elliptically-polarized. An ellipsometer generally measures the changes in the state of polarization and includes a monochromatic light source, collimators, a polarizer with or without a quarter wavelength plate, a surface upon which the subject sample is placed, an analyzer and a photo detector.

The polarization of the light reflecting off a sample is measured and analyzed to determine the variations in that polarization from the incident light. For this analysis, spectroscopic ellipsometers generally use a polarizer, a quarter wavelength plate, and an analyzer. The polarizer and the analyzer are rotated to obtain the respective angles for the polarizer and the analyzer at which the reflected light from the sample is extinguished by the analyzer. From these angles, the variables of polarized light can be calculated, such as the phase difference (delta, $\Delta$) and the amplitude-reflection ratio angle (psi, $\Psi$). In addition, the ellipsometer can measure changes in position of the reflected beam due to reflection from a second surface of the subject sample.

Spectroscopic ellipsometry techniques may be used to determine the thickness of thin films on solid materials, such as an oxide film thickness on a semiconductor material. Spectroscopic ellipsometry techniques, devices and analyses use numerical approximations to determine certain properties of the sample material, such as the dielectric constant and complex index of refraction.

In one embodiment, using a variable angle spectroscopic ellipsometer, the wavelength of light used can be in the range of from about 300 nm to about 1000 nm, and measurements can typically be performed at several angles normal to the sample, for example, at 70°, 75° and 80°. A Cauchy model can be used to calculate film thickness, the dispersion curves for the index of refraction and extinction coefficient for the films.

In one embodiment, the spectroscopic ellipsometer is capable of determining the complex permittivity, $\epsilon$, of a sample material at a single frequency from reflectance intensity measurements at that frequency. Such a spectroscopic ellipsometer is described in U.S. Pat. No. 5,625,455 (the '455 patent). The ellipsometer described in the '455 patent operates over a range of optical wavelengths from the infrared (about 7000 nm) to the ultraviolet (about 200 nm). In the '455 patent, an ellipsometry method for determining optical and spectroscopic properties of a material is described which includes steps of subjecting a material to an incident radiation having a determined elliptical polarization state; measuring a resultant radiation from the material due to interaction with the incident radiation; creating digitized intensity data for the resultant radiation; and utilizing the digitized intensity data to determine a complex index of refraction or a complex dielectric constant for the material. Thus, as disclosed in more detail in the '455 patent, in one embodiment of the present invention, the permittivity can be directly obtained by the spectroscopic ellipsometer.

In addition to a direct measurement method, in one embodiment of the present invention, the data obtained from the spectroscopic ellipsometer may be used to construct standard curves for plots of the K value versus the refractive index for high-K, standard-K and composite dielectric materials. By knowing the refractive index of the dielectric material film, K can be obtained from such a standard curve. The data may be stored in the memory or hard drive of the microprocessor, and by use of the simple equation $$y=mx+b$$

where y is the K value, m is the slope, x is the refractive index, and b is the y-intercept, the K value can be obtained.

The process maybe illustrated for an example in which a composite dielectric material film is to be formed, in which the composite dielectric material is hafnium silicate, which has the approximate general formula $Hf_xSi_yO_4$. Hafnium silicate may be considered to include the elements of silicon dioxide, $SiO_2$ and hafnium dioxide, $HfO_2$. Thus, for example, if a hafnium silicate, having the general formula $Hf_xSi_yO_4$, includes approximately equal portions of hafnium and silicon, then $x \cong y \cong 1$. As in known, the K value of $SiO_2$ is about 4, and the K value of $HfO_2$ is about 20, as shown in the above table of dielectric materials. The K value of the resulting composite dielectric material, $Hf_xSi_yO_4$, depends on the exact stoichiometry of hafnium and silicon, and by varying the stoichiometry, the K value of the resulting hafnium silicate can be selected and controlled.

For example, based on the above K values, if x=y=1, then the K value of the resulting hafnium silicate would be expected to be about 12. If x=0.75 and y=1.25, the K value of the resulting hafnium silicate would be expected to be about 10.5. If x=1.25 and y=0.75, the K value of the resulting hafnium silicate would be expected to be about 14. If each of these stoichiometric variations of hafnium silicate are prepared, the K values, refractive indices and any other ellipsometric parameter may be determined and plotted, each parameter yielding a line in accordance with the equation y=mx+b. This information can then be used to automatically control the deposition process in order to obtain hafnium silicate (or any other dielectric material, whether high-K, standard-K or composite) having a desired K value.

Process for Depositing Dielectric Films and Controlling Dielectric Constant

The present invention further relates to a process of depositing a dielectric material film while controlling the dielectric constant based on in situ feedback on the quality, thickness and dielectric constant of the nascent film obtained by a spectroscopic ellipsometer integrated with the device used for deposition of the dielectric material. In one embodiment, the dielectric material is a high-K dielectric material. In another embodiment, the dielectric material is a standard-K dielectric material. In another embodiment, the dielectric material is a composite dielectric material, as defined above. It should be understood that, while the process is sometimes described in terms of depositing a high-K dielectric material, it is applicable to deposition of any dielectric material.

Figure 4:
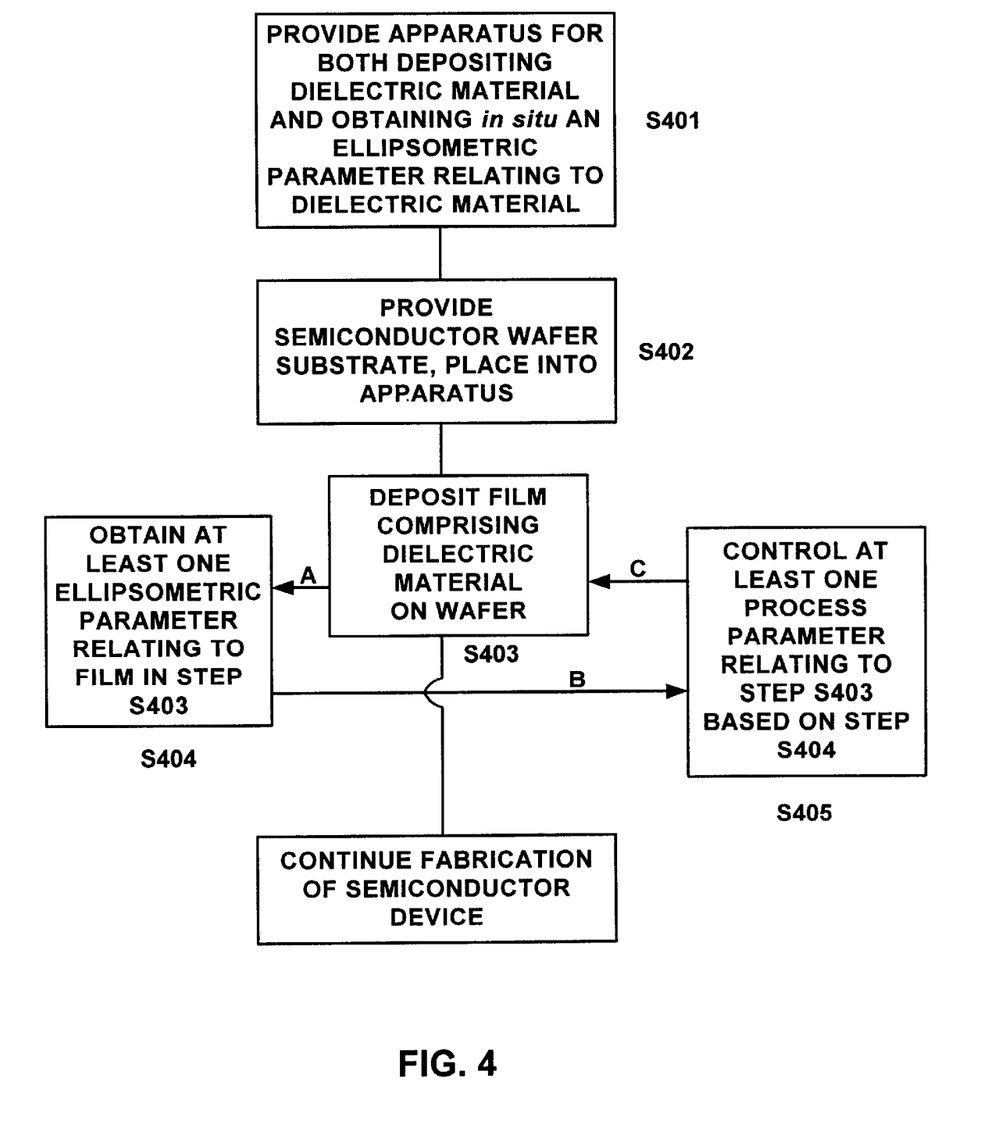
FIG. 4 is a schematic flow diagram showing the basic steps in a process of depositing a dielectric material film in accordance with the present invention.

Details of an exemplary process in accordance with the present invention are set forth below. FIG. 4 provides an exemplary schematic process flow diagram of the steps in one embodiment of a method in accordance with the present invention. The specific examples provided herein are intended to explain the invention, but are not intended to limit the scope of the invention, which is defined by the attached claims.

In one embodiment, the present invention relates to a method of controlling a process of depositing a dielectric material film, including steps of initiating a process of depositing a dielectric material film under at least one controllable initial condition in an apparatus comprising a dielectric material deposition chamber and a spectroscopic ellipsometer; and measuring in situ, by the spectroscopic ellipsometer, at least one ellipsometric parameter of the dielectric material film during the process of depositing the film. In one embodiment, the dielectric material is a high-K dielectric material. In another embodiment, the dielectric material is a standard-K dielectric material. In another embodiment, the dielectric material is a composite dielectric material. In one embodiment, the composite dielectric material is a silicate, including elements of a silicon-containing standard-K dielectric material and elements of a high-K dielectric material. In one embodiment, the composite dielectric material is an aluminate, including elements of an aluminum-containing dielectric material and elements of a high-K dielectric material.

Thus, in this embodiment, the present invention measures at least one ellipsometric parameter, such as the refractive index or the dielectric constant, of a dielectric material during the process of depositing the dielectric material. The process of depositing a dielectric material may be, for example, a CVD method, such as any one of LPCVD, MOCVD, ALCVD or RTCVD. Thus, in one embodiment, the deposition device described below is a CVD device. In another embodiment, the deposition device is any one of a LPCVD, MOCVD, ALCVD or RTCVD device. The in situ measurement of these properties allows control and adjustment of the deposition process, allowing the process to selectively deposit a dielectric material having a selected K value and/or having a selected composition of dielectric materials.

In the first step of the process of the present invention, shown in FIG. 4 as Step S401, there is provided an apparatus including a first device for depositing a dielectric material; a second device configured to obtain in situ at least one ellipsometric parameter relating to at least one of refractive index and dielectric constant of the dielectric material during deposition of the dielectric material in the first device; a processor for receiving the at least one ellipsometric parameter from the second device and outputting information relating to at least one process parameter; and a controller for receiving information from the processor and controlling operating conditions of the first device based on the information relating to the at least one process parameter. It is to be understood that, as used herein, "controlling" at least one operating parameter includes starting, stopping, changing and holding constant the at least one operating parameter. In one embodiment, the first device is a CVD device, and the second device is a spectroscopic ellipsometer.

Figure 1:
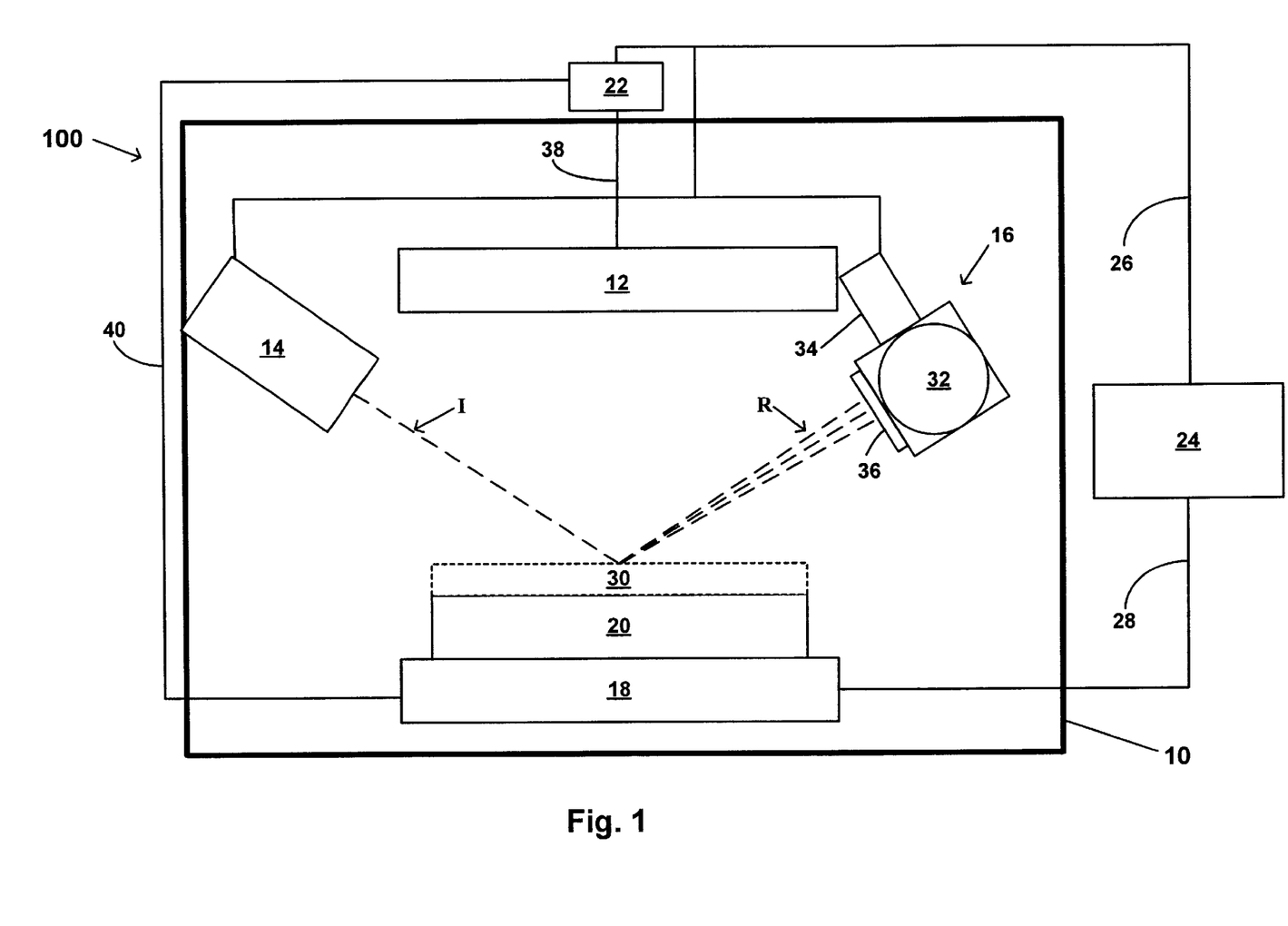
FIG. 1 is a schematic diagram view of an exemplary apparatus, including a high-K dielectric material deposition chamber, a spectroscopic ellipsometer and a controller, in accordance with the present invention.

An exemplary highly schematic view of an apparatus 100 for depositing a dielectric material having a controlled K value in accordance with the present invention is shown in FIG. 1. The apparatus 100 includes an enclosed deposition chamber 10, which may be used, for example, for depositing a dielectric material and, in one embodiment, for depositing a high-K dielectric material, on a substrate such as a semiconductor substrate.

As shown in FIG. 1, the deposition chamber 10 includes a deposition device 12, a spectroscopic ellipsometer including, inter alia, an illumination assembly 14 and a detection assembly 16, a support portion 18 related to the deposition device 12, and a substrate 20 placed on the support portion 18. The apparatus 100 includes a deposition controller 22 which controls the deposition device 12. The apparatus 100 further includes a central controller 24, which is linked via communication lines 26, 28 to the deposition controller 22 and to the spectroscopic ellipsometer assemblies 14 and 16. The communication line 26 provides communication between the central controller 24 and both the illumination assembly 14 and the detection assembly 16 of the spectroscopic ellipsometer, and between the central controller 24 and the deposition controller 22. The deposition controller 22 controls the deposition process via communication lines 38 and 40, which connect respectively to the deposition device 12 and the support portion 18. The communication line 28 provides communication between the central controller 24 and the support portion 18 of the deposition device 12, for purposes such as monitoring the positions of the support portion 18 and of the substrate 20.

In operation of the deposition chamber 10, under the control of the deposition controller 22, the deposition device 12 deposits a dielectric material film 30, for example, a high-K dielectric material film, on the substrate 20. The dielectric material film 30 is shown in dashed lines in FIG. 1 to indicate that this film 30 is formed in the deposition chamber 10 during the process of carrying out the present invention.

As indicated, the spectroscopic ellipsometer shown schematically in FIG. 1 includes the illumination assembly 14 and the detection assembly 16. The spectroscopic ellipsometer is configured to obtain data in situ relating to measurement or determination of at least one of refractive index and dielectric constant, during deposition of a dielectric material in the deposition chamber 10. The illumination assembly 14 includes a light source, for example, a laser (not shown in detail). The illumination assembly 14 outputs a light beam, I, which strikes the dielectric material film 30 and is reflected at least partially as at least one reflected beam, R, to the detection assembly 16. As discussed in more detail below, a part of the incident light beam I may not be reflected. The detection assembly 16 is mounted in association with the illumination assembly 14, and is positioned appropriately to receive the at least one reflected beam R from the surface of the dielectric material film 30.

In one exemplary embodiment (not shown in detail), the illumination assembly 14 includes a laser source capable of outputting laser light at an appropriate power and at a selected wavelength in the optical range. The illumination assembly may include an objective optical assembly which focuses the laser beam to a spot having a selected size on the film 30. In one embodiment, a polarization beam splitter and a half-wave plate are placed between the laser (which produces a polarized output beam) and the objective assembly, to more precisely control the polarization state of the illumination beam. The polarizer passes light of a defined polarization, while the half wave plate rotates the direction of polarization. The illumination assembly 14 may further include an active half wave retarder, such as a liquid crystal half wave retarder, which may be controlled by the central controller 24 to cause the illumination assembly 14 to provide a selected s- or p-polarization state. These elements of the illumination assembly 14 are merely exemplary, any illumination assembly appropriate for use with a spectroscopic ellipsometer in association with the selected deposition apparatus being acceptable for use with the present invention.

As shown in FIG. 1, in one exemplary embodiment, the detection assembly 16 includes an integrating sphere 32 having a small aperture, with the aperture directed toward the point at which the light beam is reflected from the dielectric material film 30. The detection assembly 16 further includes a photodetector 34 mounted in relation to the sphere to detect the level of collected light entering the sphere. The detection assembly 16 may further include a filter assembly 36. The filter assembly 36 may be, for example, a baffled passage or other filter to shield the detection assembly collector from light other than that of the reflected beam. In another embodiment, the filter assembly 36 is a fixed or variable polarizer to selectively pass a particular state of polarization. In another embodiment, the filter assembly 36 is a narrow bandpass interference filter. These elements of the detection assembly 16 are merely exemplary, any detection assembly appropriate for use with a spectroscopic ellipsometer in association with the selected deposition apparatus being acceptable for use in the present invention.

Referring still to FIG. 1, the central controller 24 includes a memory in which is stored appropriate information and encoded instructions including, for example, information relating to quality, thickness, refractive indices, dielectric constants and K values for dielectric materials, control parameters for operation of the deposition apparatus, and standard curves and look-up tables containing any of the foregoing or other related information. Other information and control instructions may be stored as appropriate. The central controller 24 may further include a microprocessor programmed to receive data from the detection assembly 16 and from the support 18, relating to the nature and condition of the dielectric material 30, programmed to output information and/or instructions to the deposition controller 22, to the illumination source 14 and to the detection assembly 16 and appropriate code for carrying out calculations and providing the foregoing functions. Thus, the central controller 24 receives data relating to at least one of the refractive index and the dielectric constant obtained by the spectroscopic ellipsometer, and in one embodiment, including data relating to the quality and thickness of the dielectric material, and provides control of the deposition process based on the data received and the coding with which it is programmed.

As described above, in one embodiment, the central controller 24 is a processor for receiving the data relating to measurement or determination of the at least one of refractive index and dielectric constant from the second device and outputting information relating to process parameters. The central controller 24 may include additional components, such as input-output hardware and software, a microprocessor, a RAM, a hard drive, etc.

The deposition controller 22 controls operation of the deposition process carried out in the chamber 10 by the deposition device 12. The deposition controller 22 controls operating conditions of the deposition chamber 10 and the deposition device 12, for example, temperature, pressure, time of operation, and the flow of reactants and carrier gas into the deposition chamber 10. As noted and further disclosed below, the deposition chamber 10 may be, for example, a CVD chamber. The deposition controller 22 receives information from the central controller 24 and adjusts the operating conditions of the deposition chamber 10 based on the information relating to process parameters obtained from the central controller 24.

In the second step of the process of the present invention, shown in FIG. 4 as Step S402, the semiconductor substrate 20 is provided, and is placed in the deposition chamber 10 on the support 18, as shown in FIG. 1. The semiconductor substrate may be any appropriately selected semiconductor substrate known in the art. In one embodiment, the semiconductor substrate is a bulk silicon substrate. In one embodiment, the semiconductor substrate is a silicon-on-insulator semiconductor substrate. In another embodiment, the semiconductor substrate is a p-doped silicon substrate. Suitable semiconductor substrates include, for example, bulk silicon semiconductor substrates, silicon-on-insulator (SOI) semiconductor substrates, silicon-on-sapphire (SOS) semiconductor substrates, and semiconductor substrates formed of other materials known in the art. The present invention is not limited to any particular type of semiconductor substrate.

It is noted that while described separately, the following steps S403, S404 and S405 are carried out together, as indicated in FIG. 4. In one embodiment, at least a portion of each of the steps S403, S404 and S405 is carried out simultaneously with the other steps. One or more of the steps may be carried out on an intermittent basis (.e.g., step S404, described below), as will be understood by a person of skill in the art.

In the third step of the process of the present invention, shown in FIG. 4 as Step S403, a dielectric material film 30 is deposited on the surface of the semiconductor substrate 20. In one embodiment, during the deposition process, the dielectric constant, K, of the dielectric material film 30 is determined. The determination may be made by measuring the dielectric constant of the dielectric material film 30 directly in an appropriate apparatus, or by measuring the refractive index of the dielectric material film 30 and calculating therefrom the dielectric constant, or by use of look-up tables or a standard curve.

In one embodiment, the dielectric material film 30 comprises a standard-K dielectric material. In one embodiment, the dielectric material film 30 comprises a composite dielectric material. In one embodiment, the dielectric material film comprises at least one high-K dielectric material, which forms a high-K dielectric material film 30.

The dielectric material film 30 may be deposited by any method known in the art, and, in embodiments including a high-K dielectric material, may include any high-K material which is appropriate for use with a semiconductor device. The high-K dielectric film 30 may comprise, for example, any one of a variety of known high-K dielectric materials, such as hafnium oxide, yttrium oxide, lanthanum oxide, and combinations of such high-K dielectric materials with standard-K dielectric materials (e.g., $SiO_2$), such as hafnium silicate, $HfSiO_4$. Suitable exemplary high-K dielectric materials include those disclosed in the above table-and associated-disclosure, and described in detail below.

The dielectric materials may be deposited by any appropriate method known in the art. In one embodiment, the dielectric material is deposited by CVD. In one embodiment, the dielectric material may be deposited by any one of LPCVD, MOCVD, ALCVD or RTCVD. Thus, as noted above, in one embodiment, the deposition device 12 may be any one of a LPCVD, MOCVD, ALCVD or RTCVD device.

In one embodiment, the high-K dielectric material includes at least one of $ZrO_2$, $HfO_2$, $Al_2O_3$, $Y_2O_3$, $La_2O_3$, silicates of one or more of $ZrO_2$, $HfO_2$, $Al_2O_3$, $Y_2O_3$, $La_2O_3$ or aluminates of one or more of $ZrO_2$, $HfO_2$, $Y_2O_3$, $La_2O_3$. In another embodiment, the high-K dielectric material includes at least one of hafnium oxide ($HfO_2$), zirconium oxide ($ZrO_2$), tantalum oxide ($Ta_2O_5$), barium titanate ($BaTiO_3$), titanium dioxide ($TiO_2$), cerium oxide ($CeO_2$), lanthanum oxide ($La_2O_3$), lanthanum aluminum oxide ($LaAlO_3$), lead titanate ($PbTiO_3$), strontium titanate ($SrTiO_3$), lead zirconate ($PbZrO_3$), tungsten oxide ($WO_3$), yttrium oxide ($Y_2O_3$), bismuth silicon oxide ($Bi_4Si_2O_{12}$), barium strontium titanate (BST) ($Ba_{1-x}Sr_xTiO_3$), PMN ($PbMg_xNb_{1-x}O_3$), PZT ($PbZr_xTi_{1-x}O_3$), PZN ($PbZn_xNb_{1-x}O_3$), and PST ($PbSc_xTa_{1-x}O_3$). In addition to the foregoing high-K dielectric materials, other high-K dielectric materials, for example, ferroelectric high-K dielectric materials such as lead lanthanum titanate, strontium bismuth tantalate, bismuth titanate and barium zirconium titanate may be suitably used in the present invention. Other high-K dielectric materials known in the art, including, for example binary and ternary oxides having K values of about 10 or higher, also may be used in the present invention.

In one embodiment, the high-K dielectric material has a K value in the range from about 10 to about 2000. In another embodiment, the high-K dielectric material has a K value in the range from about 10 to about 200, and in yet another embodiment, the K value is from about 20 to about 50. In one embodiment, the composite dielectric material has a K in the range from about 4 to about 50, and in another embodiment from about 4 to about 20, and in another embodiment from about 4 to about 10.

Figure 2:
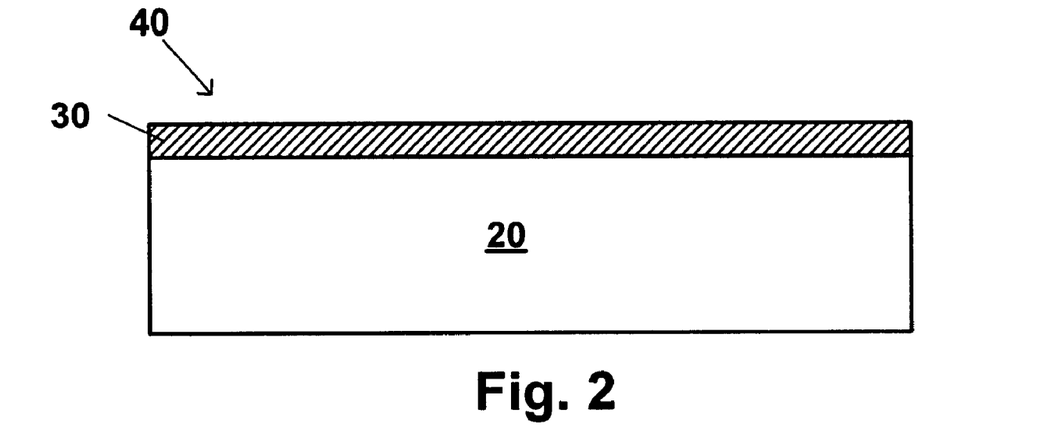
FIG. 2 is a schematic cross-sectional view of a semiconductor wafer with a layer of a dielectric material applied thereto in accordance with the present invention.
Figure 3:
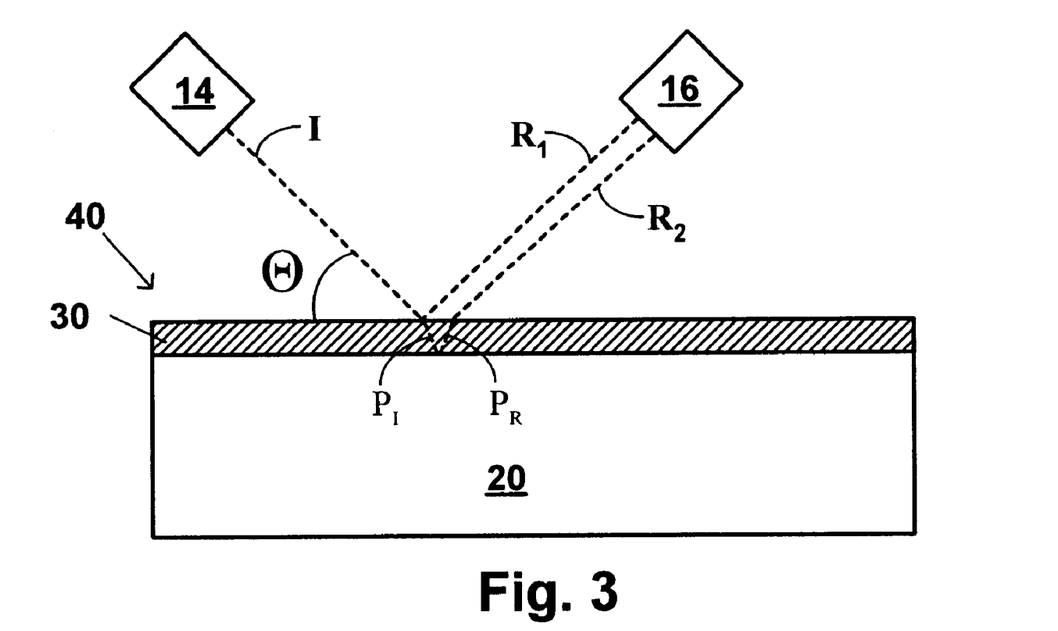
FIG. 3 is a schematic cross-sectional view of a semiconductor wafer with a layer of a dielectric material applied thereto which is undergoing measurement by a device such as a spectroscopic ellipsometer.

FIGS. 2 and 3 show a semiconductor wafer 40, including the semiconductor substrate 20 and the dielectric material film 30, after deposition of the dielectric material film, i.e., at the completion of step S403. The dielectric material film 30 is shown in FIG. 1 in dashed lines, since it is initially not present, and is formed during the process of the present invention. Although only a single high-K dielectric material film 30 is shown in FIGS. 1–3, it is understood that multiple films may be included in the dielectric material film 30. In an embodiment including a plurality of dielectric material films, each of the dielectric material films may be deposited in accordance with the present invention.

The fourth step of the process of the present invention, shown in FIG. 4 as Step S404, is measuring, during the depositing step, at least one ellipsometric parameter relating to the at least one of refractive index and dielectric constant of the film. This step is carried out during the third step and the fifth step, i.e., the steps S403 and S405, depositing the high-K dielectric material film and controlling at least one parameter relating to the process.

FIG. 3 is a schematic cross-sectional view of a semiconductor wafer 40 with a dielectric material film 30 applied to the semiconductor substrate 20 thereof, which is undergoing measurement by a device such as the spectroscopic ellipsometer described with respect to FIG. 1. FIG. 3 schematically indicates exemplary paths taken by light beams used for measuring the thickness of the dielectric material film 30.

In one embodiment, the at least one ellipsometric property is the refractive index of the dielectric material. In another embodiment, the at least one ellipsometric property is the dielectric constant, K, of the dielectric material. In another embodiment, the at least one ellipsometric property includes data relating to the polarization state of incident and reflected light, intensity data, angle of incidence and angle of reflection of the light impinging on the dielectric material film, the principal angle of the dielectric material, and other related parameters needed for determination of refractive index and dielectric constant of the dielectric material film. In another embodiment, the ellipsometric data relates to determination of the thickness of the dielectric material film 30, which may include, inter alia, an ellipsometric property relating to the refractive index of the dielectric material film 30.

As described above, in one embodiment, the fourth step includes use of a spectroscopic ellipsometer. In one embodiment, the spectroscopic ellipsometer is a variable angle ellipsometer.

FIG. 3 schematically shows the basic elements for determination of the thickness of a film, such as the dielectric material film 30. As described above in respect to the description of the spectroscopic ellipsometer, the ellipsometer includes the illumination source 14 and the detection assembly 16. The illumination source 14 emits a light beam I, which is in one embodiment a laser beam, as shown in FIG. 3. The incident beam I has a predetermined polarization and intensity. The incident beam I strikes the surface of the dielectric material film 30 at an angle of incidence $\Theta$. A first portion of the incident beam I is reflected from the surface of the film 30, as indicated in FIG. 3 by first reflected beam $R_1$. The first reflected beam $R_1$ enters the detector assembly 16, and is detected. The polarization of the first reflected beam $R_1$ has been changed by the interaction of the incident laser beam I with the surface, and the intensity of the beam $R_1$ has been reduced with respect to the incident beam I.

A second portion of the incident beam I, designated as beam $P_I$, penetrates the surface of the film 30, as indicated in FIG. 3. Since the refractive index of the film 30 differs from that of the space above the film 30, the angle at which the beam $P_I$ travels through the film 30 differs from the angle of incidence $\Theta$. A portion of the beam $P_I$ is reflected from the lower surface of the film 30, indicated as a reflected beam $P_R$ in FIG. 3. The reflected beam $P_R$ reaches the upper surface of the film 30 and exits the upper surface as the second reflected beam $R_2$. The path which the second reflected beam $R_2$ travels is similar to, but may not be exactly parallel to, the path followed by the first reflected beam $R_1$ from the surface of the film 30 to the detector assembly 16. However, due to the change in its path while traversing the film 30, the path of the second reflected beam $R_2$ has been shifted with respect to the path of the first reflected beam $R_1$. The second reflected beam $R_2$ enters the detector assembly 16, and is detected. The polarization of the reflected beam $R_2$ has been changed by the passage of the incident beam I through the film 30, and the intensity of the beam $R_2$ has been reduced with respect to the incident beam I. The differences between the beams $R_1$ and $R_2$ may be used, for example, to obtain information relating to the thickness of the dielectric material film 30. Thus, in this embodiment, the ellipsometric parameter relates to the refractive index which in turn relates to the thickness of the dielectric material film 30.

In one embodiment, the spectroscopic ellipsometer detects at least one of the polarization, intensity, position and other parameters (as noted above) of the reflected beams $R_1$ and $R_2$. This information, as described above, may be used to determine the quality, thickness and K value of the dielectric material film 30. In one embodiment, the ellipsometer outputs the information relating to these parameters directly to a controller for controlling at least one parameter relating to the step of depositing a dielectric material film. In one embodiment, the ellipsometer outputs the information relating to these parameters to the central controller 24, shown in FIG. 1, and the central controller 24 then carries out the fifth step of the present invention.

The fifth step of the process of the present invention, shown in FIG. 4 as Step S405, includes controlling, during the depositing step, at least one process parameter relating to the depositing step based on the measured at least one of refractive index and dielectric constant of the film. This step actually is carried out during the third and fourth steps, i.e., the steps S403 and S404, depositing the high-K dielectric material film and measuring the at least one of refractive index and dielectric constant of the film. As shown in FIG. 4, these three steps are carried out in coordination with each other.

The step of controlling, during the depositing step, at least one process parameter relating to the depositing step, includes starting, stopping, increasing, decreasing and holding constant any variable parameter relating to operation of the deposition process of the dielectric material deposited in the deposition chamber 10. Such parameters include, for example, chamber pressure, partial pressure and flows of dielectric precursor materials, partial pressure and flows of reactant gases such as oxygen, nitric oxide, nitrous oxide, partial pressure and flows of carrier gases such as nitrogen, argon or helium, chamber, substrate and other temperatures, and time of operation of the deposition process.

As used herein, the term dielectric precursor material means any agent which, when provided to a suitable deposition device, either directly or through reaction with another chemical species, for ms a dielectric material film on the substrate. For example, when the dielectric material is silicon dioxide, the dielectric precursor material may be silane, tetraethylsilane, dichlorosilane and any other known precursor which, reacted with an appropriate oxygen source, reacts to form silicon dioxide. In one embodiment, a precursor for hafnium oxide is hafnium tetra-t-butoxide, and in another embodiment, a precursor for zirconium oxide is zirconium tetra-t-butoxide.

Thus, the fifth step of the present invention, in one embodiment, includes operating the central controller 24 to obtain information from the spectroscopic ellipsometer, and to use that information to determine appropriate settings, such as those listed above, in the deposition device 12, via the deposition controller 22. The central controller 24 may carry out calculation of the equations described above, or other, related equations used to determine at least one of the refractive index and the dielectric constant of the dielectric material film 30 which is being deposited in the present method.

The interrelationship of steps S403, S404 and S405 is shown schematically in FIG. 4. Therein, it can be seen that, while the step S403, depositing a film comprising a dielectric material is proceeding, the spectroscopic ellipsometer, in step S404, is collecting data relating to at least one ellipsometric parameter relating to the film being formed in step S403. The transfer of this information relating to step S403 is indicated by arrow A in FIG. 4. The ellipsometer outputs this information or, in one embodiment, processes the information and outputs the processed information, relating to the at least one ellipsometric parameter to the controller, as shown in arrow B in FIG. 4. The controller, in step S405, controls at least one process parameter relating to step S403 based on the information obtained from step S404. In one embodiment, step S405 is carried out by a microprocessor programmed to receive the ellipsometric information from step S404 and to output control signals or information to the deposition process in step S403. The transfer of control information relating to control of the at least one process parameter in step S403 is schematically shown by arrow C in FIG. 4.

Thus, as shown in FIG. 4, the present invention includes both an apparatus and a method for depositing a dielectric material film, including steps of initiating a process of depositing a dielectric material film under at least one controllable initial condition in an apparatus including a dielectric material deposition chamber and a spectroscopic ellipsometer; and measuring, by the spectroscopic ellipsometer, at least one ellipsometric parameter of the dielectric material film during the process of depositing the film.

An exemplary process may be described using the example mentioned above, in which the process of the present invention is employed to form a composite dielectric material film of hafnium silicate. As noted above, as the proportion of $HfO_2$ increases with respect to the proportion of $SiO_2$, the K value of the resulting composite dielectric material film increases. The deposition process may be initiated using estimated conditions based on historical information relating to the K value desired and the materials of interest. This information may be inputted directly to the central controller either manually or from an outside control source. As precursor materials are fed to the process, the hafnium silicate film 30 begins to form on the substrate 20. As the hafnium silicate film 30 is formed, the spectroscopic ellipsometer collects data relating to the film 30. This data is sent to the central controller 24. The K value of the hafnium silicate film 30 is calculated by the central controller 24 based on the received data. Based on the calculated K value of the resulting film 30, the central controller 24 directs the deposition controller 22 to vary the flows of precursor materials to control the deposition process. Thus, for example, if the K value needs to be increased, the relative amount of the high-K precursor fed to the process is increased with respect to the silicon-containing precursor. Conversely, if the K value needs to be increased, the relative amount of the high-K precursor fed to the process is decreased with respect to the silicon-containing precursor. As the deposition proceeds, the thickness may be monitored based on data obtained by the spectroscopic ellipsometer and provided thereby to the central controller 24, and the deposition process terminated when the desired thickness is obtained. Thus, there is provided a method of depositing a dielectric material film, including initiating a process of depositing a dielectric material film under at least one controllable initial condition in an apparatus comprising a dielectric material deposition chamber and a spectroscopic ellipsometer; and measuring in situ, by the spectroscopic ellipsometer, at least one ellipsometric parameter of the dielectric material film during the process of depositing the film.

While the invention has been described in conjunction with specific embodiments herein, it is evident that many alternatives, modifications and variations will be apparent to those skilled in the art in light of the foregoing description. Accordingly it is intended to embrace all such alternatives and modifications in variations as for within the spirit and broad scope of the appended claims.

Industrial Applicability

According to the present invention, a solution to the problem of control of quality thickness and K value of dielectric materials in situ is provided, during fabrication of semiconductor devices including high-K dielectric materials. The present invention allows obtaining a selected equivalent oxide thickness by providing for in situ control of both the physical thickness and the K value of the dielectric material. The present invention responds to the need for a process of manufacturing semiconductor devices with a high-K dielectric material film that improves process control of the quality, thickness and K value of dielectric material films, and particularly in high-K dielectric material films, while avoiding unduly expensive and time-consuming physical measurement and/or electrical testing of such dielectric films.

What is claimed is:

1. A method of depositing a dielectric material film on a semiconductor substrate, comprising:

initiating a process of depositing a dielectric material film on a semiconductor substrate under at least one controllable initial condition in an apparatus comprising a dielectric material deposition chamber and a spectroscopic ellipsometer; and measuring in situ, by the spectroscopic ellipsometer, at least one ellipsometric parameter of the dielectric material film during the process of depositing the film.

2. The method of claim 1, wherein the method further comprises controlling the at least one initial condition based on the at least one ellipsometric parameter.

3. The method of claim 2, wherein the controlling comprises adjusting stoichiometry of at least one high-K precursor and oxygen supplied to the deposition chamber to obtain a desired dielectric constant, K.

4. The method of claim 2, wherein the controlling comprises adjusting relative quantities of at least two dielectric material precursors supplied to the deposition chamber to obtain a desired dielectric constant, K.

5. The method of claim 4, wherein the at least two dielectric material precursors comprise at least one high-K dielectric material precursor and at least one of an aluminum-containing dielectric material precursor and a silicon-containing dielectric material precursor.

6. The method of claim 1, wherein the at least one ellipsometric parameter is at least one of refractive index or dielectric constant, K.

7. The method of claim 1, wherein the high-K dielectric material deposition chamber is a CVD chamber.

8. The method of claim 7, wherein the CVD is one of LPCVD, MOCVD, ALCVD or RTCVD.

9. The method of claim 1, wherein the spectroscopic ellipsometer is a variable angle spectroscopic ellipsometer.

10. The method of claim 1, wherein the high-K dielectric material is at least one of hafnium oxide ($HfO_2$), zirconium oxide ($ZrO_2$), tantalum oxide ($Ta_2O_5$), barium titanate ($BaTiO_3$), titanium dioxide ($TiO_2$), cerium oxide ($CeO_2$), lanthanum oxide ($La_2O_3$), lanthanum aluminum oxide ($LaAlO_3$), lead titanate ($PbTiO_3$), strontium titanate ($SrTiO_3$), lead zirconate ($PbZrO_3$), tungsten oxide ($WO_3$), yttrium oxide ($Y_2O_3$), bismuth silicon oxide ($Bi_4Si_2O_{12}$), barium strontium titanate (BST) ($Ba_{1-x}Sr_xTiO_3$), PMN ($PbMg_xNb_{1-x}$), PZT ($PbZr_xTi_{1-x}$), PZN ($PbZn_xNb_{1-x}O_3$) and PST ($PbSc_xTa_{1-x}O_3$), ferroelectric high-K dielectric materials, binary and ternary oxides having K values of about 10 or higher, silicates of one or more thereof, aluminates of one or more thereof, or mixtures of two or more thereof.

11. A method for depositing a high-K dielectric material on a semiconductor substrate, comprising:

providing an apparatus comprising both a device for depositing a dielectric material and a device configured to measure in situ at least one ellipsometric parameter relating to at least one of refractive index and dielectric constant of the dielectric material;

placing a semiconductor substrate into the apparatus;

depositing on the semiconductor substrate a film comprising a high-K dielectric material;

measuring in situ, during the depositing step, the elipsometric parameter relating to at least one of refractive index and dielectric constant of the dielectric material film; and controlling, during the depositing step, at least one process parameter relating to the depositing step based on the ellipsometric parameter relating to at least one of refactive index and dielectric constant of the dielectric material film.

12. The method of claim 11, wherein the controlling comprises adjusting stoichiometry of at least one dielectric material precursor and oxygen supplied to the device for depositing a dielectric material.

13. The method of claim 11, wherein the controlling comprises adjusting relative quantities of at least two dielectric material precursors supplied to the device for depositing a dielectric material.

14. The method of claim 13, wherein the at leat two dielectric material precursors comprise at least one high-K dielectric material precursor and at least one of an aluminum-containing dielectric material precursor and a silicon-containing dielectric material precursor.

15. The method of claim 11, wherein the device for depositing a dielectric material is a CVD device.

16. The method of claim 15, wherein the CVD device is one of a LPCVD, MOCVD, an ALCVD or a RTCVD device.

17. The method of claim 11, wherein the device for measuring in situ at least one ellipsometric parameter relating to at least one of refractive index and dielectric constant of the high-K dielectric material is a spectroscopic ellipsometer.

18. The method of claim 11, wherein the dielectric material is at least one of hafnium oxide ($HfO_2$), ziconium oxide ($ZrO_2$), tantalum oxide ($Ta_2O_5$), barium titanate ($BaTiO_3$), titanium dioxide ($TiO_2$), cerium oxide ($CeO_2$), lanthanum oxide ($La_2O_3$), lanthanum aluminum oxide ($LaAlO_3$), lead titanate ($PbTiO_3$), strontium titanate ($SrTiO_3$), lead zirconate ($PbZrO_3$), tungsten oxide ($WO_3$), yttrium oxide ($Y_2O_3$), bismuth silicon oxide ($Bi_4Si_2O_{12}$), barium strontium titanate (BST) ($Ba_{1-x}Sr_xTiO_3$), PMN ($PbMg_xNb_{1-x}O_3$), PZT ($PbZr_xTi_{1-x}O_3$), PZN ($PbZn_xNb_{1-x}O_3$), and PST ($PbSc_xTa_{1-x}O_3$), ferroelectric high-K dielectric materials, binary and ternary oxides having K values of about 10 or higher, silicates of one or more thereof, aluminates of one or more thereof, or mixtures of two or more thereof.

19. A method of depositing a dielectric material film on a semiconductor substrate, comprising:

initiating a process of depositing a dielectric material film on the semiconductor substrate under at least one controllable initial condition in an apparatus comprising a dielectric material deposition chamber and a spectroscopic ellipsometer;

measuring in situ, by the spectroscopic ellipsometer, at least one ellipsometric parameter of the dielectric material film during the process of depositing the film; and controlling, during the depositing step, the at least one controllable initial condition based on the elipsometric parameter relating to at least one of refractive index and dielectric constant of the dielectric material film.

20. A method as in claim 19, wherein the controlling comprises adjusting stoichiometry of at least one dielectric material precursor and oxygen supplied to the device for depositing a dielectric material.

21. The method of claim 19, wherein the controlling comprises adjusting relative quantities of at least two dielectric material precursors supplied to the device for depositing a dielectric material.

* * * * *